US009345878B2

(12) United States Patent
DiGiore et al.

(10) Patent No.: US 9,345,878 B2
(45) Date of Patent: May 24, 2016

(54) SYSTEM AND METHOD FOR COMPENSATING FOR SHIFTING OF NEUROSTIMULATION LEADS IN A PATIENT

(75) Inventors: Andrew DiGiore, Santa Monica, CA (US); Kristen Jaax, Santa Clara, CA (US); Courtney Lane, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1707 days.

(21) Appl. No.: 12/495,442

(22) Filed: Jun. 30, 2009

(65) Prior Publication Data
US 2010/0331922 A1      Dec. 30, 2010

(51) Int. Cl.
*A61N 1/08*          (2006.01)
(52) U.S. Cl.
CPC .............. *A61N 1/08* (2013.01); *A61N 2001/083* (2013.01)
(58) Field of Classification Search
CPC ......... A61B 5/061; A61B 5/063; A61B 5/085
USPC ...................................................... 607/2, 11
See application file for complete search history.

(56) References Cited

U.S. PATENT DOCUMENTS

| | | | |
|---|---|---|---|
| 5,197,467 | A | 3/1993 | Steinhaus et al. |
| 6,261,247 | B1 | 7/2001 | Ishikawa et al. |
| 6,516,227 | B1 | 2/2003 | Meadows et al. |
| 6,609,029 | B1 | 8/2003 | Mann et al. |
| 6,741,892 | B1 | 5/2004 | Meadows et al. |
| 6,993,384 | B2 | 1/2006 | Bradley et al. |
| 7,062,330 | B1 | 6/2006 | Boveja et al. |
| 7,076,307 | B2 | 7/2006 | Boveja et al. |
| 7,228,171 | B2 | 6/2007 | Lesser et al. |
| 7,285,118 | B1 | 10/2007 | Lozano |
| 7,539,538 | B2 | 5/2009 | Parramon et al. |
| 2003/0139781 | A1 | 7/2003 | Bradley et al. |
| 2003/0153959 | A1* | 8/2003 | Thacker ............. A61N 1/36071 607/48 |
| 2004/0199235 | A1 | 10/2004 | Younis |
| 2005/0004611 | A1 | 1/2005 | Edwards et al. |
| 2005/0267546 | A1 | 12/2005 | Parramon et al. |

(Continued)

FOREIGN PATENT DOCUMENTS

| | | |
|---|---|---|
| EP | 0576114 A2 | 12/1993 |
| EP | 0576114 B1 | 3/2001 |

(Continued)

*Primary Examiner* — Michael Kahelin
*Assistant Examiner* — Minh Duc Pham
(74) *Attorney, Agent, or Firm* — Schwegman Lundberg & Woessner, P.A.

(57) ABSTRACT

A method for determining a change in position of a neurostimulation lead relative to a stimulation target tissue of a patient is provided. The method comprises implanting a first proximity sensor on a surface of the patient, implanting a second proximity sensor on the surface of the patient, measuring a change in a distance between the first and second proximity sensors, and inferring the change in position of the lead relative to the stimulation target tissue from the measured change in distance. The method further comprises inferring an increase in a distance between the lead and the stimulation target tissue when the distance between the first and second proximity sensors increases. The method also comprises conveying electrical stimulation energy to therapeutically stimulate the stimulation target tissue, and modulating a stimulation parameter in response to the measured change in distance.

14 Claims, 9 Drawing Sheets

(56) References Cited

U.S. PATENT DOCUMENTS

| | | | |
|---|---|---|---|
| 2006/0206035 A1* | 9/2006 | Friedrichs | A61B 5/1135 600/534 |
| 2006/0206165 A1 | 9/2006 | Jaax et al. | |
| 2006/0224187 A1 | 10/2006 | Bradley et al. | |
| 2006/0224222 A1 | 10/2006 | Bradley et al. | |
| 2006/0235484 A1 | 10/2006 | Jaax et al. | |
| 2007/0049988 A1 | 3/2007 | Carbunaru et al. | |
| 2007/0112403 A1 | 5/2007 | Moffitt et al. | |
| 2007/0112404 A1 | 5/2007 | Mann et al. | |
| 2007/0129770 A1 | 6/2007 | Younis | |
| 2007/0239057 A1 | 10/2007 | Pu et al. | |
| 2007/0255085 A1 | 11/2007 | Kishawi et al. | |
| 2008/0188909 A1 | 8/2008 | Bradley | |
| 2008/0281379 A1* | 11/2008 | Wesselink | A61B 5/107 607/60 |
| 2009/0132009 A1* | 5/2009 | Torgerson | A61N 1/3708 607/61 |
| 2009/0157155 A1 | 6/2009 | Bradley | |
| 2010/0010585 A1* | 1/2010 | Davis | A61N 1/36135 607/62 |

FOREIGN PATENT DOCUMENTS

| | | |
|---|---|---|
| EP | 1868680 A2 | 10/2006 |
| EP | 1948292 A2 | 7/2008 |
| WO | WO 03/028521 A2 | 4/2003 |
| WO | WO 2006/107848 A2 | 10/2006 |
| WO | WO 2007/059343 A2 | 5/2007 |
| WO | WO 2008/095185 A1 | 8/2008 |
| WO | WO 2009/079600 A2 | 6/2009 |

* cited by examiner

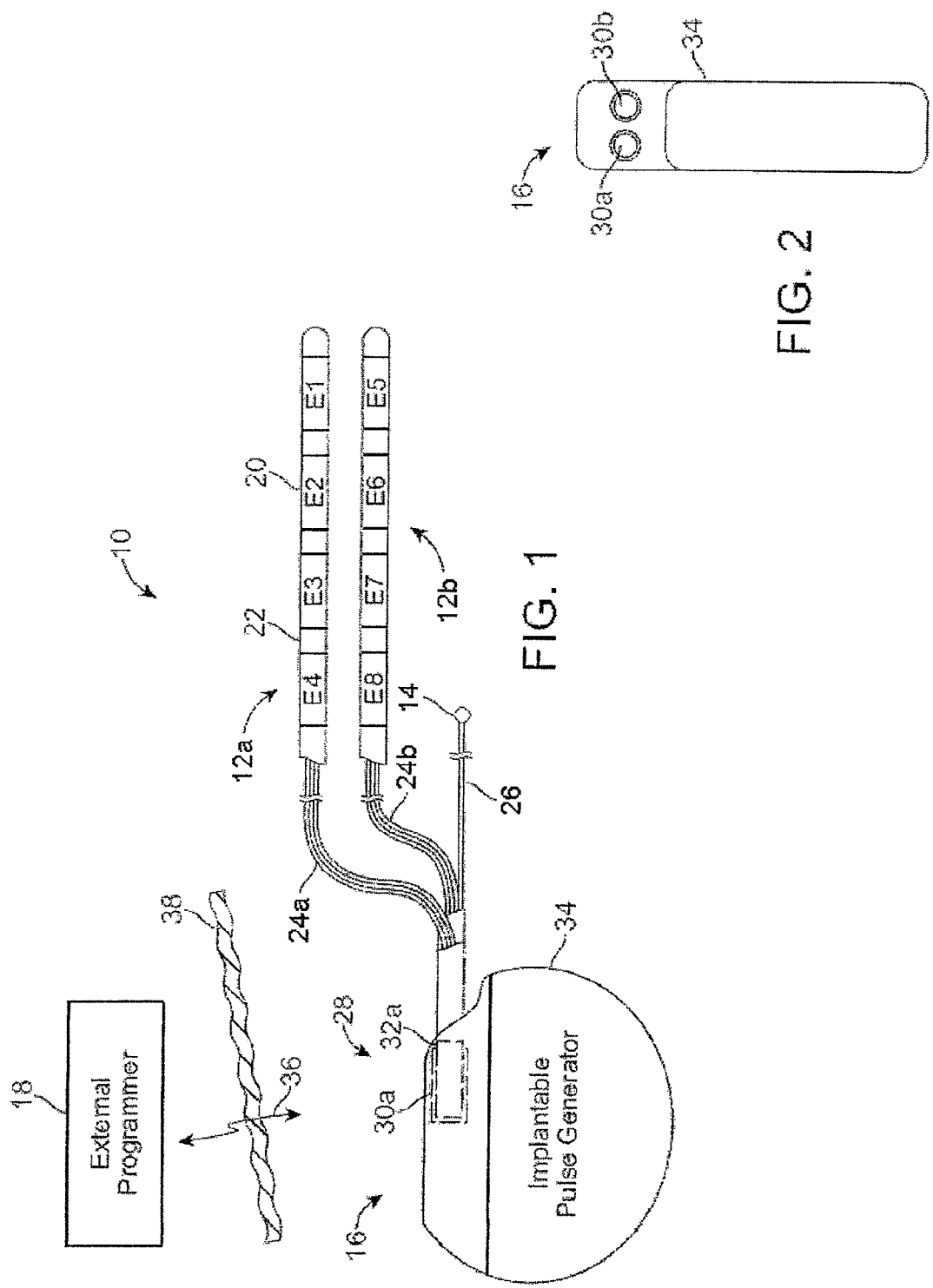

SYSTEM AND METHOD FOR COMPENSATING FOR SHIFTING OF NEUROSTIMULATION LEADS IN A PATIENT

FIELD OF THE INVENTION

The present invention relates to tissue stimulation systems, and more particularly, to a system and method for measuring lead shifts in a patient implanted with a tissue stimulation system.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Specifically, Occipital Nerve Stimulation (ONS), in which leads are implanted in the tissue over the occipital nerves, has shown promise as a treatment for various headaches, including migraine headaches, cluster headaches, and cervicogenic headaches.

Each of these implantable neurostimulation systems typically includes an electrode lead, having one or more electrodes, implanted at the desired stimulation site and an implantable pulse generator (IPG) implanted remotely from the stimulation site, but coupled either directly to the electrode lead or indirectly to the electrode lead via a lead extension. Thus, electrical pulses can be delivered from the IPG to the electrode lead to stimulate the tissue and provide the desired efficacious therapy to the patient.

Significantly, precise positioning of the leads proximal to the targets of stimulation is critical to the success of the therapy. If the leads shift position, the stimulation target tissue may no longer be appropriately stimulated. For example, when electrical stimulation devices, such as occipital nerve stimulators, are implanted in a patient, the leads and the IPG are anchored to the tissue. However, during postural changes and patient movement, the leads (and/or other system components) may shift. Notably, in lead shifting, as opposed to lead migration, the leads return to their previous position after the patient returns to a neutral/resting position.

During lead shifting, the patient feels a change in stimulation sensations and possibly no stimulation at all. Changes in stimulation sensation may be drastic, causing jolting or a piercing sensation. When lead shifting eliminates paresthesia, i.e. the tingling sensation that replaces pain during successful treatment, the patient may revert back to their pain state, or, in the case of ONS, generate a migraine headache.

Changes in stimulation may be explained by the lead moving back and forth over the targeted nerve, while removal of stimulation therapy may be explained by the lead shifting off of the nerve. The entire lead may not shift off of the nerve. Instead, one stimulating electrode may shift off of the nerve or shift too far away from the nerve for effective stimulation. For instance, when an ONS patient's head is rotated, implanted stimulating electrodes may no longer be properly positioned over the targeted occipital nerves.

Changes in stimulation with posture change can also be caused by changes in the thickness of the tissue between the lead and the targeted nerve. The thickness of this intervening tissue may decrease when postural changes, such as neck movements, stretch the tissue or increase when postural changes bunch up the tissue. This change in thickness of the intervening tissue, in turn, moves the lead closer to or farther from the targeted nerve, resulting in changes in stimulation.

Lead shifting can be overcome by reprogramming the tissue stimulation system based on the new position of the leads to restore therapy. However, determining the presence and degree of lead shifting based paresthesia is imprecise. Also, attempting to reprogram the leads based on paresthesia locations is challenging.

Alternatively, a determination of the position of implanted leads can be made using X-ray or fluoroscopy. Disadvantageously, X-ray and fluoroscopy require expensive equipment, significant time, and appropriate medical facilities, most of which are not readily available. Moreover, if the leads shift after a fluoroscopic image is taken, this image may no longer be valid, thereby resulting in poor patient outcomes due to inappropriate or unexpected stimulation effects.

There, thus, remains a need for an improved method and system for compensating for lead shifting during patient movement.

SUMMARY OF THE INVENTION

In accordance with a first aspect of the present inventions, a method for determining a change in position of a neurostimulation lead relative to a stimulation target tissue of a patient is provided. The method comprises implanting a first proximity sensor on a surface of the patient, implanting a second proximity sensor on the surface of the patient, measuring a change in a distance between the first and second proximity sensors, and inferring the change in position of the lead relative to the stimulation target tissue from the measured change in distance. The method further comprises inferring an increase in a distance between the lead and the stimulation target tissue when the distance between the first and second proximity sensors increases. The method also comprises conveying electrical stimulation energy to therapeutically stimulate the stimulation target tissue, and modulating a stimulation parameter in response to the measured change in distance.

The method further comprises automatically modulating the stimulation parameter in response to the inferred change in position. In one optional method, modulating a stimulation parameter in response to the inferred change in position comprises increasing an amplitude of a stimulation current when the distance between the first and second proximity sensors increases. In another optional method, modulating a stimulation parameter comprises adjusting an amplitude of the stimulus applied to selected electrodes during the conveyance of the stimulation energy. The method also comprises conveying electrical stimulation energy via a combination of electrodes to therapeutically stimulate the stimulation target tissue via electrodes. In still another optional method, the step of modulating a stimulation parameter comprises changing the combination of the electrodes.

In accordance with a second aspect of the present inventions, a system for determining a change in position of a neurostimulation lead relative to a stimulation target tissue of a patient is provided. The system comprises a first proximity sensor configured to be placed on a surface of the patient, a second proximity sensor configured to be placed on the surface of the patient, monitoring circuitry configured to measure a change in a distance between the first and second proximity sensors, and processing circuitry configured to infer the change in position of the lead relative to the stimulation target tissue from the measured change in distance. In one embodiment, the processing circuitry is configured to infer an increase in a distance between the lead and the stimulation target tissue when the distance between the first and second proximity sensors increases.

The system also includes an implantable pulse generator configured to be coupled to the lead and to convey electrical stimulation energy to therapeutically stimulate the stimulation target tissue, and control circuitry configured to modulate a stimulation parameter in response to the inferred change in position. In another embodiment, the control circuitry is configured to increase an amplitude of a stimulation current when the distance between the first and second proximity sensors increases. In yet another embodiment, the control circuitry is configured to automatically modulate the stimulation parameter in response to the measured change in distance. In still another embodiment, the control circuitry is configured to adjust an amplitude of the stimulus applied to selected electrodes during the conveyance of the stimulation energy in response to the inferred change in position. The system further comprises a plurality of electrodes configured to be coupled to the lead and to convey electrical stimulation energy to therapeutically stimulate the stimulation target tissue via a combination of electrodes, whereby the control circuitry is configured to change the combination of the electrodes in response to the inferred change in position.

In accordance with a third aspect of the present inventions, a method for determining a change in position of a neurostimulation lead relative to a stimulation target tissue of a patient is provided. The method comprises implanting the lead having a first proximity sensor disposed thereon into the patient, implanting a second proximity sensor on a surface of the patient, measuring a change in alignment between the first and second proximity sensors, and inferring the change in position of the lead relative to the stimulation target tissue from the measured change in alignment. The method further comprises inferring an increase in a distance between the lead and the stimulation target tissue when the first and second proximity sensors become misaligned. The method also comprises conveying electrical stimulation energy to therapeutically stimulate the stimulation target tissue, and modulating a stimulation parameter in response to the inferred change in position. The method also comprising conveying electrical stimulation energy via a combination of electrodes to therapeutically stimulate the stimulation target tissue via electrodes. Modulating a stimulation parameter can be performed in the same manner described above.

In accordance with a fourth aspect of the present inventions, a system for determining a change in position of a neurostimulation lead relative to a stimulation target tissue of a patient is provided. The system comprises a lead configured to be placed into the patient, a first proximity sensor disposed on the lead, a second proximity sensor configured to be placed on a surface of the patient, monitoring circuitry configured to measure a change in alignment between the first and second proximity sensors, and processing circuitry configured to infer the change in position of the lead relative to the stimulation target tissue from the measured change in alignment. In one embodiment, the processing circuitry is configured to infer an increase in a distance between the lead and the stimulation target tissue when the first and second proximity sensors become misaligned. The system further comprises an implantable pulse generator configured to be coupled to the lead and to convey electrical stimulation energy to therapeutically stimulate the stimulation target tissue, and control circuitry configured to modulate a stimulation parameter in response to the inferred change in position. In another embodiment, the control circuitry is configured to increase an amplitude of a stimulation current when the first and second proximity sensors become misaligned. The system also comprises a plurality of electrodes configured to be coupled to the lead and to convey electrical stimulation energy to therapeutically stimulate the stimulation target tissue via a combination of electrodes. The system modulates stimulation parameters in the same manner described above.

In accordance with a fifth aspect of the present inventions, a method for determining a change in position of a neurostimulation lead relative to a stimulation target tissue of a patient is provided. The method comprises implanting the lead having a voltage sensor disposed thereon into the patient, implanting a plurality of magnets on a surface of the patient, measuring a change in voltage at the voltage sensor in response to movement of the magnets relative to the voltage sensor, and inferring the change in position of the lead relative to the stimulation target tissue from the measured change in voltage. The method further comprises conveying electrical stimulation energy to therapeutically stimulate the stimulation target tissue, and modulating a stimulation parameter in response to the inferred change in position. The method also comprises inferring a distance between the neurostimulation lead and the stimulation target tissue. The method further comprises conveying electrical stimulation energy via a combination of electrodes to therapeutically stimulate the stimulation target tissue via electrodes. Modulating a stimulation parameter can be performed in the same manner described above.

In accordance with a sixth aspect of the present inventions, a system for determining a change in position of a neurostimulation lead relative to a stimulation target tissue of a patient is provided. The system comprises a lead configured to be placed into the patient, a voltage sensor disposed on the lead, a plurality of magnets configured to be placed on a surface of the patient, monitoring circuitry configured to measure a change in voltage at the voltage sensor in response to movement of the magnets relative to the voltage sensor, and processing circuitry configured to infer the change in position of the lead relative to the stimulation target tissue from the measured change in voltage. The system further comprises an implantable pulse generator configured to be coupled to the lead and to convey electrical stimulation energy to therapeutically stimulate the stimulation target tissue, and control circuitry configured to modulate a stimulation parameter in response to the inferred change in position. The system also comprises a plurality of electrodes configured to be coupled to the lead and to convey electrical stimulation energy to therapeutically stimulate the stimulation target tissue via a combination of electrodes. The system modulates stimulation parameters in the same manner described above.

In accordance with a seventh aspect of the present inventions, a method for determining a change in position of a neurostimulation lead relative to a stimulation target tissue of a patient is provided. The method comprises measuring a change in capacitance at the lead in response to a change in thickness of tissue adjacent the lead, and inferring the change in position of the lead relative to the stimulation target tissue from the measured change in capacitance. The method further comprises implanting a capacitor within the patient, where the capacitor comprises a plurality of capacitor plates that measure the change in capacitance, and a compressible dielectric material disposed between the capacitor plates, wherein the capacitor plates move closer to each other when the dielectric material is compressed and the capacitor plates move farther from each other when the dielectric material is expanded.

One optional method comprises inferring an increase in a distance between the lead and the stimulation target tissue when the capacitance decreases. Another optional method, comprises inferring a decrease in a distance between the lead and the stimulation target tissue when the capacitance increases. The method also comprises conveying electrical stimulation energy to therapeutically stimulate the stimulation target tissue, and modulating a stimulation parameter in response to the measured change in capacitance. Modulating a stimulation parameter can be performed in the same manner described above.

In accordance with an eighth aspect of the present inventions, a system for determining a change in position of a neurostimulation lead relative to a stimulation target tissue of a patient is provided. The system comprises an implantable capacitor, monitoring circuitry configured to measure a change in capacitance at the capacitor, and processing circuitry configured to infer the change in position of the lead relative to the stimulation target tissue from the measured change in capacitance. The capacitor comprises a plurality of capacitor plates that measure the change in capacitance, and a compressible dielectric material disposed between the capacitor plates, where the capacitor plates move closer to each other when the dielectric material is compressed and the capacitor plates move farther from each other when the dielectric material is expanded. In one embodiment, the processing circuitry is configured to infer an increase in a distance between the lead and the stimulation target tissue when the capacitance decreases. In another embodiment, the processing circuitry is configured to infer a decrease in a distance between the lead and the stimulation target tissue when the capacitance increases.

The system further comprises an implantable pulse generator configured to be coupled to the lead and to convey electrical stimulation energy to therapeutically stimulate the stimulation target tissue, and control circuitry configured to modulate a stimulation parameter in response to the inferred change in position. The system also comprises a plurality of electrodes configured to be coupled to the lead and to convey electrical stimulation energy to therapeutically stimulate the stimulation target tissue via a combination of electrodes. Modulating a stimulation parameter can be performed in the same manner described above.

In accordance with a ninth aspect of the present inventions, a method for determining a change in position of a neurostimulation lead relative to a stimulation target tissue of a patient is provided. The method comprises measuring a change in temperature at the lead in response to a change in thickness of tissue adjacent the lead, and inferring the change in position of the lead relative to the stimulation target tissue from the measured change in temperature. One optional method comprises inferring an increase in a distance between the lead and the stimulation target tissue when the temperature decreases. Another optional method comprises inferring a decrease in a distance between the lead and the stimulation target tissue when the temperature increases. The method further comprises conveying electrical stimulation energy to therapeutically stimulate the stimulation target tissue, and modulating a stimulation parameter in response to the measured change in temperature. Modulating a stimulation parameter can be performed in the same manner described above.

In accordance with a tenth aspect of the present inventions, a system for determining a change in position of a neurostimulation lead relative to a stimulation target tissue of a patient is provided. The system comprises an implantable temperature sensor, monitoring circuitry configured to measure a change in temperature at the lead in response to a change in thickness of tissue adjacent the lead, and processing circuitry configured to infer the change in position of the lead relative to the stimulation target tissue from the measured change in temperature. In one embodiment, the processing circuitry is configured to infer an increase in a distance between the lead and the stimulation target tissue when the temperature decreases. In another embodiment, the processing circuitry is configured to infer a decrease in a distance between the lead and the stimulation target tissue when the temperature increases. The system further comprises an implantable pulse generator configured to be coupled to the lead and to convey electrical stimulation energy to therapeutically stimulate the stimulation target tissue, and control circuitry configured to modulate a stimulation parameter in response to the measured change in temperature. The system modulates stimulation parameters in the same manner described above.

In accordance with an eleventh aspect of the present inventions, a method for determining a change in position of a neurostimulation lead relative to an occipital nerve is provided. The method comprises measuring a change in a parameter adjacent the lead, and inferring the change in position of the lead relative to the occipital nerve from the measured change in the parameter. The method further comprises inferring a change in a distance between the lead and the occipital nerve from the measured change in the parameter, conveying electrical stimulation energy to therapeutically stimulate the occipital nerve, and modulating a stimulation parameter in response to the inferred change in position. Modulating a stimulation parameter can be performed in the same manner described above.

In accordance with a twelfth aspect of the present inventions, a system for determining a change in position of a lead of an occipital nerve stimulation device relative to an occipital nerve is provided. The system comprises a sensor configured to measure a change in a parameter adjacent the lead, and processing circuitry configured to infer the change in position of the lead relative to the occipital nerve from the measured change in the parameter. The system further comprises an implantable pulse generator configured to be coupled to the lead and to convey electrical stimulation energy to therapeutically stimulate the occipital nerve, and control circuitry configured to modulate a stimulation parameter in response to the inferred change in position. The system modulates stimulation parameters in the same manner described above.

In accordance with a thirteenth aspect of the present inventions, a method for determining a change in position of a neurostimulation lead relative to a stimulation target tissue of a patient is provided. The method comprises implanting the lead with a sensor disposed thereon into the patient, conveying electrical energy from the lead into the stimulation target tissue of the patient over a period of time, measuring data from the sensor, whereby the data is modulated in response to changes in a position of the lead relative to the stimulation target tissue, analyzing the time-varying data, and tracking the changes in the position of the lead relative to the stimulation target tissue during the time period based on the analyzed time-varying data. In one optional method, the electrical energy conveyed from the lead provides therapy to the patient. In another optional method the data is one or both of capacitance data or temperature data. In still another optional method, the step of analyzing the time-varying data comprises determining a magnitude of the time-varying data.

Yet another optional method further comprises implanting a second sensor disposed on a surface of the patient, where the data is a distance between the sensor and the second sensor. Another optional method further comprises implanting a plurality of magnets on a surface of the patient, where the data is voltage data.

The method further comprises modulating a stimulation parameter in response to the changes in the position of the lead relative to the stimulation target tissue. Modulating a stimulation parameter can be performed in the same manner described above. In an alternative method, the implanted lead does not have a sensor disposed thereon and the step of implanting a second sensor is replaced with the step of implanting two proximity sensors disposed on a surface of the patient.

In accordance with a fourteenth aspect of the present inventions, a tissue stimulation system is provided. The system comprises a sensor disposed on an implantable lead, an implantable electrical stimulation device configured for being coupled to the lead, the electrical stimulation device configured for conveying electrical energy from the lead into a stimulation target tissue of a patient over a period of time and measuring data from the sensor, where the data is modulated in response to changes in a position of the lead relative to the stimulation target tissue, and a processing device configured for analyzing the time-varying data, and tracking the changes in the position of the lead relative to the stimulation target tissue during the time period based on the analyzed time-varying data. In one embodiment, the electrical energy conveyed from the lead provides therapy to the patient. In another embodiment, the data is one or both of capacitance date or temperature data. In still another embodiment, the processing device is the stimulation device. In yet another embodiment, the processing device is an external programmer configured for communicating with the stimulation device.

In one embodiment, the time-varying data analysis comprises determining a magnitude of the time-varying data. In another embodiment, the system further comprises a second sensor disposed on a surface of the patient, where the data is a distance between the sensor and the second sensor. In still another embodiment, the system further comprises a plurality of magnets disposed on a surface of the patient, where the data is voltage data. In yet another embodiment, the stimulation device is configured to modulate a stimulation parameter in response to the changes in the position of the lead relative to the stimulation target tissue. The system modulates stimulation parameters in the same manner described above. In an alternative embodiment, two proximity sensors disposed on a surface of the patient replace the sensor disposed on the implantable lead and the second sensor.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1 is plan view of one embodiment of a occipital nerve stimulation (ONS) system arranged in accordance with the present inventions;

FIG. 2 is a profile view of an implantable pulse generator (IPG) used in the ONS system of FIG. 1;

DETAILED DESCRIPTION OF THE EMBODIMENTS

Figure 3:
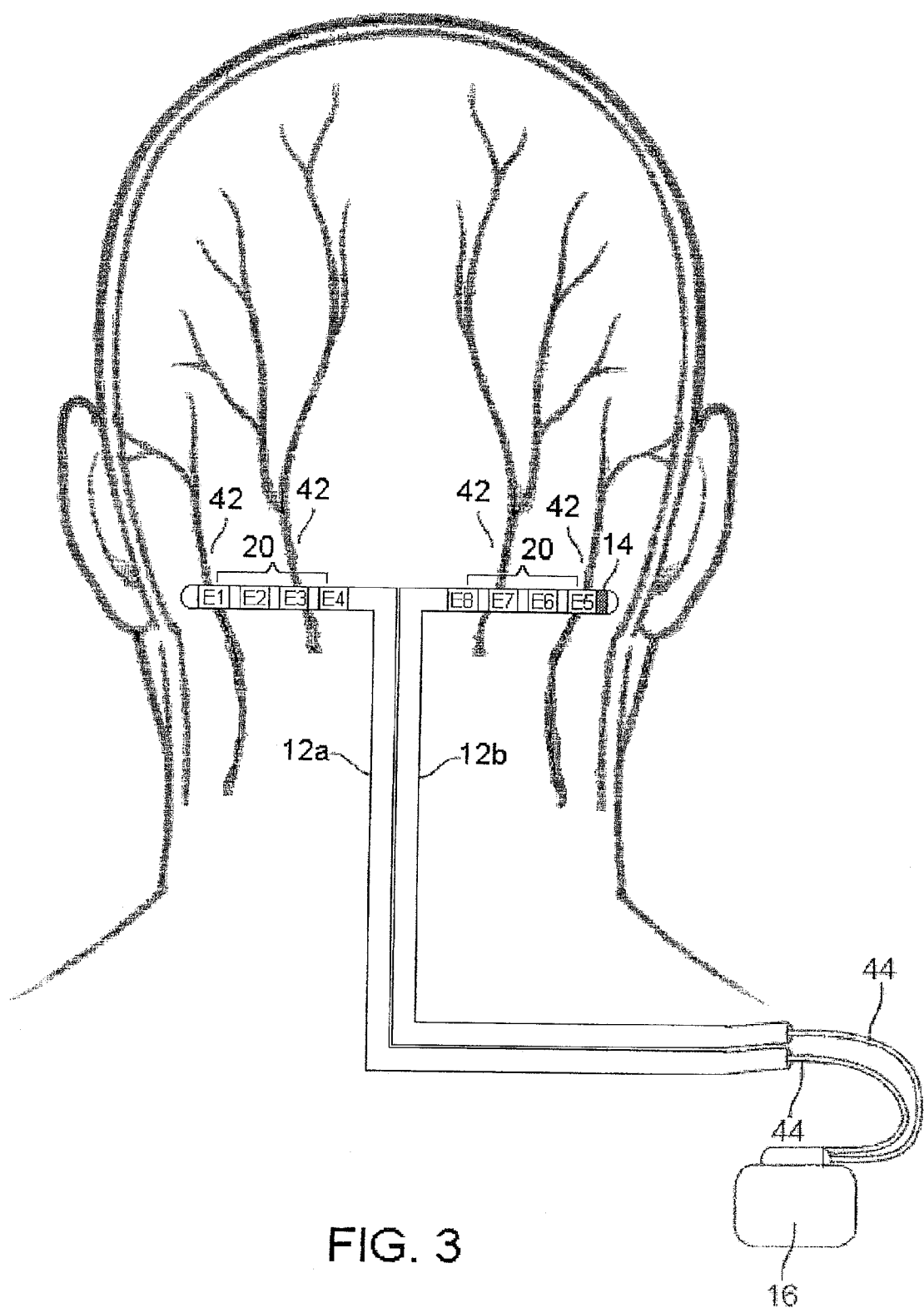
FIG. 3 is a schematic view of the ONS system of FIG. 1 in use with a patient.

The description that follows relates to an occipital nerve stimulation (ONS) system. However, it is to be understood that the while the invention lends itself well to applications in ONS, the invention, in its broadest aspects, may not be so limited. Rather, the invention may be used with any type of implantable electrical circuitry used to stimulate tissue. For example, the present invention may be used as part of a spinal cord stimulation (SCS) system, pacemaker, a defibrillator, a cochlear stimulator, a retinal stimulator, a stimulator configured to produce coordinated limb movement, a cortical and deep brain stimulator, peripheral nerve stimulator, or in any other neural stimulator configured to treat urinary incontinence, sleep apnea, shoulder sublaxation, etc.

Turning first to FIGS. 1 and 2, an exemplary ONS system 10 generally includes first and second implantable neurostimulation leads 12 (12a and 12b), one or more lead movement sensors 14 (only one shown in FIG. 1), an implantable pulse generator (IPG) 16, and an external (non-implanted) programmer 18. In the illustrated embodiment, the leads 12 are percutaneous leads and, to that end, both of the leads comprise a plurality of in-line electrodes 20 carried on a flexible body 22. Alternatively, the leads 12 may be replaced with paddle electrode leads. In the illustrated embodiment, the first lead 12a has four electrodes 20 (labeled E1-E4), and the second lead 12b includes four electrodes 20 (labeled E5-E8). The actual number of leads and electrodes will, of course, vary according to the intended application.

The IPG 16 is capable of directing electrical stimulation energy to each of the electrodes 20. To that end, the electrodes 20 of the first lead 12a are electrically connected to the IPG 16 by respective wires 24a that extend through, or are embedded in, the associated flexible lead body 22. Similarly, the electrodes 20 of the second lead 12b are electrically connected to the IPG 16 by respective wires 24b. The wires 24a, 24b are connected to the IPG 16 by way of an interface 28. The interface 28 may be any suitable device that allows the leads 12 to be removably or permanently electrically connected to the IPG 16. Such an interface may, for example, be an electromechanical connector arrangement including lead connectors 30a, 30b within the IPG 16 that are configured to mate with corresponding connectors (only connector 32a is shown) on the corresponding leads 12. Alternatively, the leads 12 can share a single connector that mates with a corresponding connector on the IPG 16. Exemplary connector arrangements are disclosed in U.S. Pat. Nos. 6,609,029 and 6,741,892, which are incorporated herein by reference. The IPG 16 includes an outer case 34 formed from an electrically conductive, biocompatible material, such as titanium and, in some instances, will function as an electrode. The case 34 forms a hermetically sealed compartment wherein the electronic and other components (described in further detail below) are protected from the body tissue and fluids.

The IPG 16 is typically programmed, or controlled, through the use of the external programmer 18. The external programmer 18 is coupled to the IPG 16 through a suitable communications link (represented by the arrow 36) that passes through the patient's skin 38. Suitable links include, but are not limited to radio frequency (RF) links, inductive links, optical links, and magnetic links. The programmer 18 or other external device may also be used to couple power into the IPG 16 for the purpose of operating the IPG 16 or replenishing a power source, such as a rechargeable battery, within the IPG 16. Once the IPG 16 has been programmed, and its power source has been charged or otherwise replenished, the IPG 16 may function as programmed without the external programmer 18 being present.

With respect to the stimulus patterns provided during operation of the ONS system 10, electrodes 20 that are selected to transmit or receive stimulation energy are referred to herein as "activated," while electrodes 20 that are not selected to transmit or receive stimulation energy are referred to herein as "non-activated." Electrical stimulation will occur between two (or more) electrodes, one of which may be the IPG case 34, so that the electrical current associated with the stimulus has a path from the energy source contained within the IPG case 34 to the tissue and a return path from the tissue to the energy source contained within the case 34. Stimulation energy may be transmitted to the tissue in a monopolar or multipolar (e.g., bipolar, tripolar, etc.) fashion.

Monopolar stimulation occurs when a selected one of the lead electrodes 20 is activated along with the case 34, so that stimulation energy is transmitted between the selected electrode 20 and case 34. Bipolar stimulation occurs when two of the lead electrodes 20 are activated as anode and cathode, so that stimulation energy is transmitted between the selected electrodes 20. For example, electrode E3 on the first lead 12a may be activated as an anode at the same time that electrode E7 on the second lead 12b is activated as a cathode. Tripolar stimulation occurs when three of the lead electrodes 20 are activated, two as anodes and the remaining one as a cathode, or two as cathodes and the remaining one as an anode. For example, electrodes E2 and E3 on the first lead 12a may be activated as anodes at the same time that electrode E6 on the second lead 12b is activated as a cathode.

The lead movement sensors 14 are electrically connected to the IPG 16 via signal wires 26, which in some embodiments, run completely inside of the electrode leads 12. As will be described in further detail below, the sensors 14 may be used to determine when a lead 12 has shifted relative to a target nerve, and in this case, an occipital nerve. Although the lead movement sensors 14 are shown to be separate from the leads 12 in FIG. 1, the sensors 14 may be located on the leads 12 depending upon the technique used to sense the lead shift. In some embodiments, the sensors 14 are ring sensors (see FIG. 3) that are mounted onto the leads 12. In still other embodiments, the sensors 14 are incorporated into the lead electrodes 20, and can be used to measure parameters, such as impedance, when the lead electrode 20 is not being used to transmit stimulation energy.

As shown in FIG. 3, the neurostimulation leads 12 are implanted subcutaneously near the intermastoid line using a percutaneous needle or other convention technique, so as to be in close proximity to the occipital nerves 42. Once in place, the electrodes 20 may be used to supply stimulation energy to the occipital nerves 42. The preferred placement of the leads 12 is such, that the electrodes 20 are adjacent, i.e., resting upon, the occipital nerve area to be stimulated. Due to the lack of space near the location where the leads 12 are implanted, the IPG 16 is generally implanted in a surgically-made pocket either in the abdomen or above the buttocks. The IPG 16 may, of course, also be implanted in other locations of the patient's body. A lead extension 44 may facilitate locating the IPG 16 away from the exit point of the leads 12.

Figure 4:
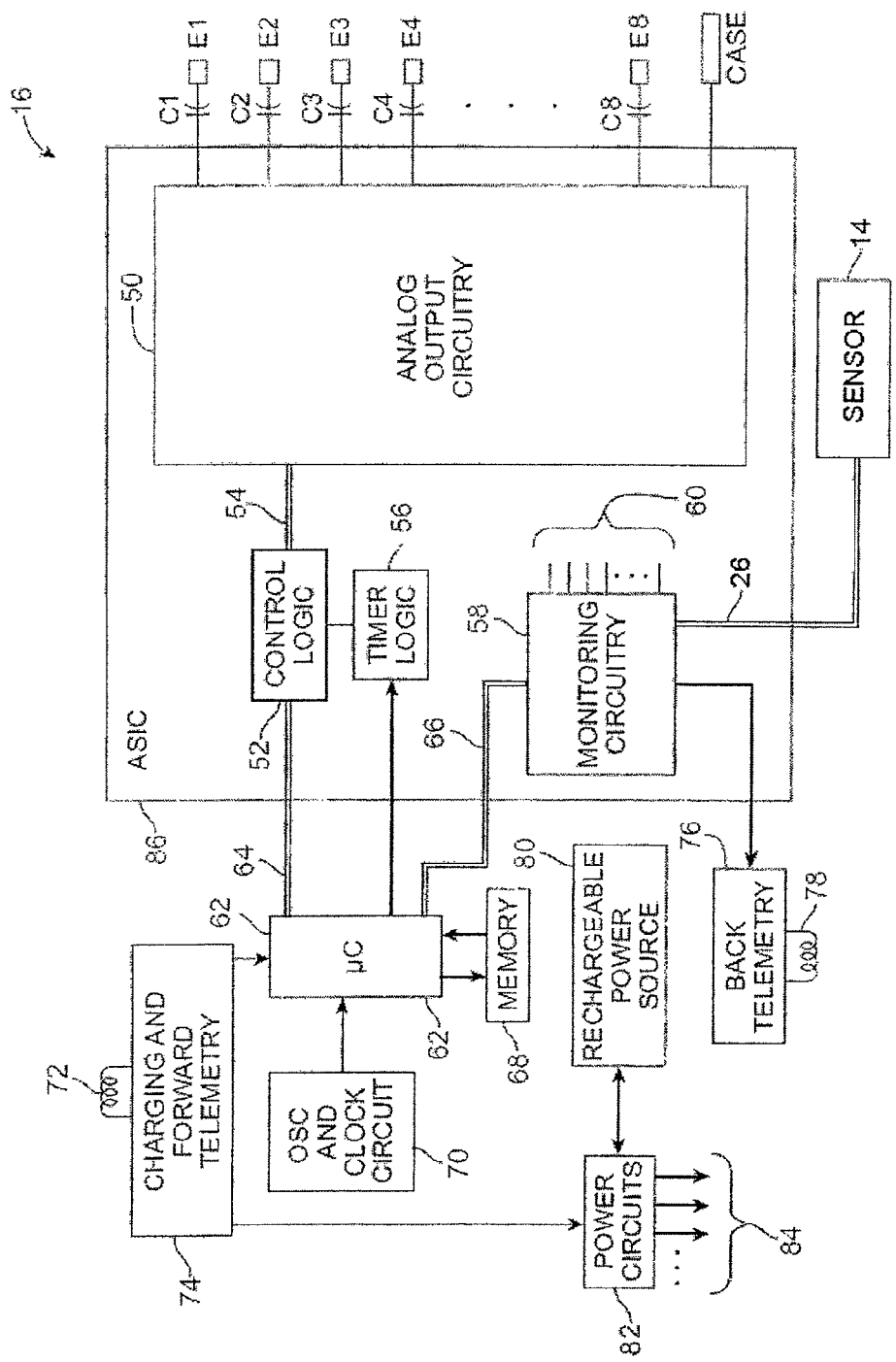
FIG. 4 is a block diagram of the internal components of the IPG of FIG. 2.

Turning next to FIG. 4, the main internal components of the IPG 16 will now be described. The IPG 16 includes analog output circuitry 50 capable of individually generating electrical stimulation pulses via capacitors C1-C8 at the electrodes 20 (E1-E8) of specified amplitude under control of control logic 52 over data bus 54. The duration of the electrical stimulation (i.e., the width of the stimulation pulses), is controlled by the timer logic circuitry 56. The analog output circuitry 50 may either comprise independently controlled current sources for providing stimulation pulses of a specified and known amperage to or from the electrodes 20, or independently controlled voltage sources for providing stimulation pulses of a specified and known voltage at the electrodes 20. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 16 also comprises monitoring circuitry 58 for monitoring the status of various nodes or other points 60 throughout the IPG 16, e.g., power supply voltages, temperature, battery voltage, and the like. Significantly, the monitoring circuitry 58 is also configured for monitoring, via the signal wires 26, the status of lead movement sensors 14 used to determine when a lead 12 has shifted relative to the occipital nerves 42. The IPG 16 further comprises processing circuitry in the form of a microcontroller (μC) 62 that controls the control logic 52 over data bus 64, and obtains status data from the monitoring circuitry 58 via data bus 66. The IPG 16 additionally controls the timer logic 56. The IPG 16 further comprises memory 68 and oscillator and clock circuit 70 coupled to the microcontroller 62. The microcontroller 62, in combination with the memory 68 and oscillator and clock circuit 70, thus comprise a microprocessor system that carries out a program function in accordance with a suitable program stored in the memory 68. Alternatively, for some applications, the function provided by the microprocessor system may be carried out by a suitable state machine.

Thus, the microcontroller 62 generates the necessary control and status signals, which allow the microcontroller 62 to control the operation of the IPG 16 in accordance with a selected operating program and stimulation parameters. In controlling the operation of the IPG 16, the microcontroller 62 is able to individually generate stimulus pulses at the electrodes 20 using the analog output circuitry 50, in combination with the control logic 52 and timer logic 56, thereby allowing each electrode 20 to be paired or grouped with other electrodes 20, including the monopolar case electrode, to control the polarity, amplitude, rate, pulse width and channel through which the current stimulus pulses are provided. The microcontroller 62 facilitates the storage of parameter data monitored by the monitoring circuitry 58 within memory 68, and also provides any computational capability needed to analyze such parameter data and/or generate lead shift information.

As briefly discussed above, the monitoring circuitry 58 is configured for monitoring when a lead 12 has shifted relative to the occipital nerves 42. In particular, any movement of lead 12 is communicated from the lead movement sensors 14 via signal wires 26 to the monitoring circuitry 58. In turn, the monitoring circuitry 58 communicates the change in distance via data bus 66 to the microcontroller 62, which uses the change in distance to determine whether either of the leads 12 has shifted relative to the occipital nerves 42. If the microcontroller 62 determines that a lead 12 has shifted, it sends a command via control logic over data bus 64 to control logic 52, which modulates stimulation parameters to compensate for the lead shift. Modulation of stimulation parameters includes varying the amplitude of a stimulation current and/or the combination of electrodes 20 through which electrical stimulation energy is conveyed to the occipital nerves 42. Other stimulation parameters that may be modulated may be, e.g., pulse width and pulse frequency. This cycle of measurement, analysis, and modulation is repeated to maintain optimal stimulation of the occipital nerves 42.

The IPG 16 further comprises an alternating current (AC) receiving coil 72 for receiving programming data (e.g., the operating program and/or stimulation parameters) from the external programmer 18 in an appropriate modulated carrier signal, and charging and forward telemetry circuitry 74 for demodulating the carrier signal it receives through the AC receiving coil 72 to recover the programming data, which programming data is then stored within the memory 68, or within other memory elements (not shown) distributed throughout the IPG 16.

The IPG 16 further comprises back telemetry circuitry 76 and an alternating current (AC) transmission coil 78 for sending informational data sensed through the monitoring circuitry 58 to the external programmer 18. The back telemetry features of the IPG 16 also allow its status to be checked. For example, when the external programmer 18 initiates a programming session with the IPG 16, the capacity of the battery is telemetered, so that the external programmer 18 can calculate the estimated time to recharge. Any changes made to the current stimulus parameters are confirmed through back telemetry, thereby assuring that such changes have been correctly received and implemented within the implant system. Moreover, upon interrogation by the external programmer 18, all programmable settings stored within the IPG 16 may be uploaded to the external programmer 18. The back telemetry features allow raw or processed parameter data and/or lead shifting information previously stored in the memory 68 to be downloaded from the IPG 16 to the external programmer 18, which information can be used to track the shifting of leads.

The IPG 16 further comprises a rechargeable power source 80 and power circuits 82 for providing the operating power to the IPG 16. The rechargeable power source 80 may, e.g., comprise a lithium-ion or lithium-ion polymer battery. The rechargeable battery 80 provides an unregulated voltage to the power circuits 82. The power circuits 82, in turn, generate the various voltages 84, some of which are regulated and some of which are not, as needed by the various circuits located within the IPG 16. The rechargeable power source 80 is recharged using rectified AC power (or DC power converted from AC power through other means, e.g., efficient AC-to-DC converter circuits, also known as "inverter circuits") received by the AC receiving coil 72. To recharge the power source 80, an external charger (not shown), which generates the AC magnetic field, is placed against, or otherwise adjacent, to the patient's skin over the implanted IPG 16. The AC magnetic field emitted by the external charger induces AC currents in the AC receiving coil 72. The charging and forward telemetry circuitry 74 rectifies the AC current to produce DC current, which is used to charge the power source 80. While the AC receiving coil 72 is described as being used for both wirelessly receiving communications (e.g., programming and control data) and charging energy from the external device, it should be appreciated that the AC receiving coil 72 can be arranged as a dedicated charging coil, while another coil, such as coil 78, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the ONS system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, the monitoring circuitry 58 is configured to monitor the status of the lead movement sensors 14, so that the microcontroller 62 can determine whether a lead 12 has moved relative to the occipital nerve 42 in which it is designed to stimulate and compensate for such lead movement.

Figure 5:
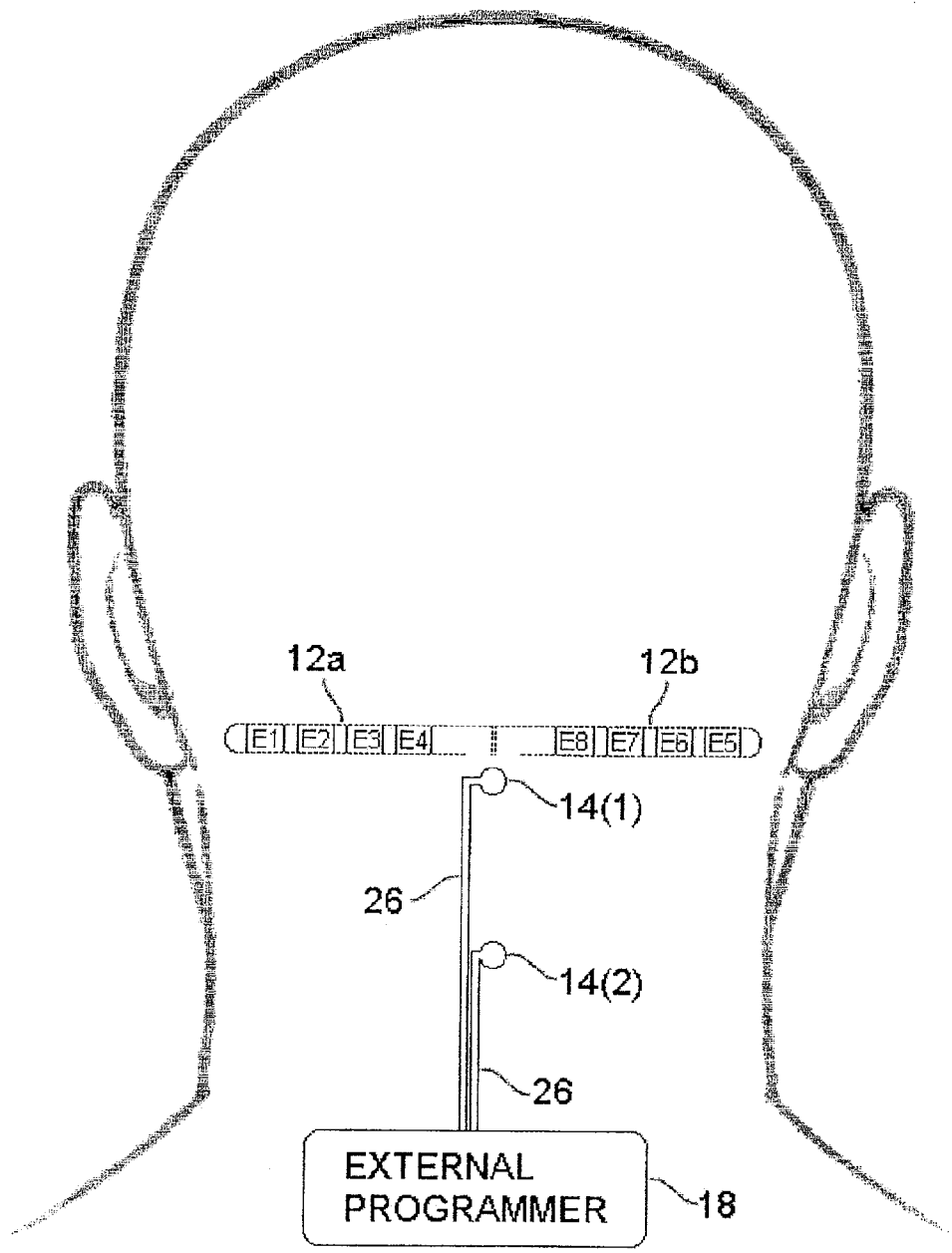
FIG. 5 is a schematic view of two proximity sensors arranged in accordance with the present inventions in use with a patient and connected to an external programmer, with the distal ends of two electrode leads shown in phantom.

In one embodiment, as shown in FIG. 5, the monitoring circuitry 58 is configured to monitor the distance between two proximity sensors 14 (a mobile sensor 14(1) and an immobile sensor 14(2)) mounted on the surface of a patient (i.e., the sensors 14 are secured to the surface of the patient in such a way that the sensors 14 resist unintentional removal). Methods for attaching devices to the surface of a patient include bonding with biocompatible adhesives, taping, and suturing. While the sensors 14(1), 14(2) are mounted on the surface of the skin, the electrodes 12a, 12b (shown in phantom) are implanted under the skin. The sensors 14(1), 14(2) are connected by signal wires 26 to an external programmer 18, which communicates wirelessly with the IPG 16 as described above.

The mobile proximity sensor 14(2) is mounted on the surface of the patient approximately overlying the occipital bone of the skull near the middles of the inferior and superior nuchal lines. The immobile proximity sensor 14(2) is mounted on the surface of the patient approximately overlying the middles of the C3 and C4 cervical vertebrae. When the patient's neck is rotated, the mobile proximity sensor 14(1) will rotate with the head away from the immobile proximity sensor 14(2), and the distance between the two proximity sensors 14 will increase. Thus, movement of the mobile proximity sensor 14(1) relative to immobile proximity sensor 14(2) is measured when the patient changes posture and the patient's skin contorts.

In general, increased distance between the proximity sensors 14 indicates an increased distance between the electrode leads 12 and the respective occipital nerves 42, while decreased distance between the proximity sensors 14 indicates a decreased distance between the electrode leads 12 and the respective occipital nerves 42. Ultimately, the correlation between the change in distance between the proximity sensors 14 and the change in distance between the electrode leads 12 and target tissue may depend on the particular application and location of stimulation. While two proximity sensors 14 are described with respect to the FIG. 5 embodiment, in other embodiments, more than two proximity sensors 14 can be mounted on the surface of the patient to provide more information about the changing position of the electrode leads 12 relative to the occipital nerves 42.

Figure 6:
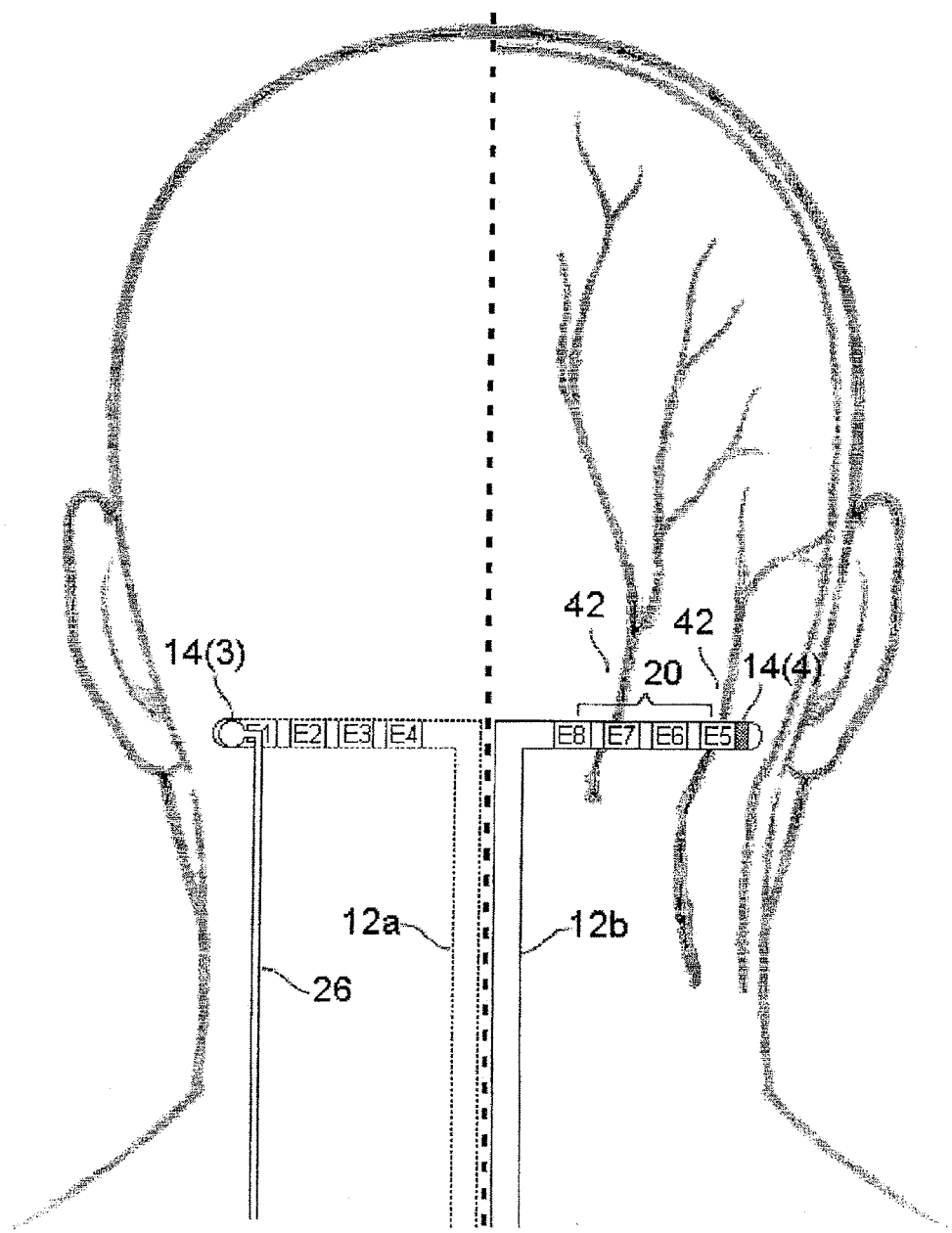
FIG. 6 is a detailed posterior view of an external proximity sensor and an internal proximity sensor of an ONS system arranged in accordance with the present inventions in use with a patient—the electrode lead on the left side of the figure is shown in phantom, and the patient's scalp on the right side of the figure has been removed for clarity.

In another embodiment, as shown in FIG. 6, the monitoring circuitry 58 is configured to monitor the distance between an external proximity sensor 14(3) mounted on the surface of a patient overlying the distal tip of each electrode lead 12 and an internal proximity sensor 14(4) attached to the distal tip of each electrode lead 12 implanted inside of the patient. The internal proximity sensor 14(4) can be a ring sensor. Thus, movement of the external proximity sensor 14(3) relative to internal proximity sensor 14(4) is measured when the patient changes posture and the patient's skin contorts. While two proximity sensors 14(3), 14(4) are described in the FIG. 6 embodiment, in other embodiments, more than two proximity sensors 14 (either mounted on the surface of the patient or attached to the electrode leads 12) can be used to provide more information about the changing position of the electrode leads 12 relative to the occipital nerves 42.

Figure 7:
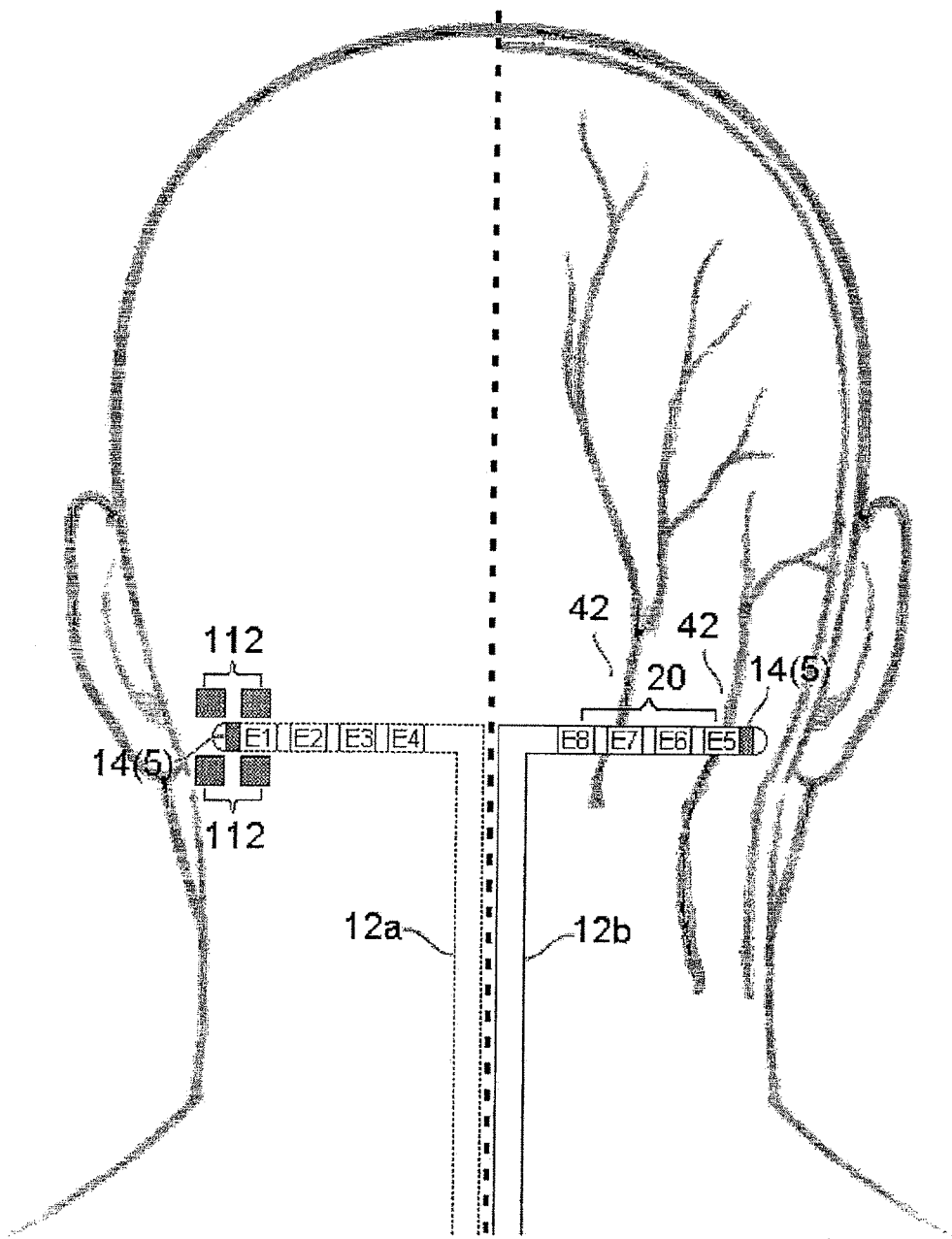
FIG. 7 is a detailed posterior view of a groups of magnets and two voltage sensors of an ONS system arranged in accordance with the present inventions in use with a patient—the electrode lead on the left side of the figure is shown in phantom, and the patient's scalp on the right side of the figure has been removed for clarity.

In yet another embodiment, as shown in FIG. 7, the monitoring circuitry 58 is configured to monitor voltages generated by voltage sensors 14(5) attached to each electrode lead 12. The voltages are generated at each sensor 14(5) in response to movement of the sensor 14(5) relative to a plurality of permanent magnets 112 mounted on the surface of the patient above the area in which the leads 12 are implanted. Notably, the voltage generated at the sensor 14(5) is a result of the Hall effect, which creates a voltage across an electrical conductor resulting from current flow in the presence of a changing magnetic field. Thus, movement of each sensor 14(5) relative to the magnets 112 are measured when the patient changes posture and the patient's skin contorts.

Figure 8:
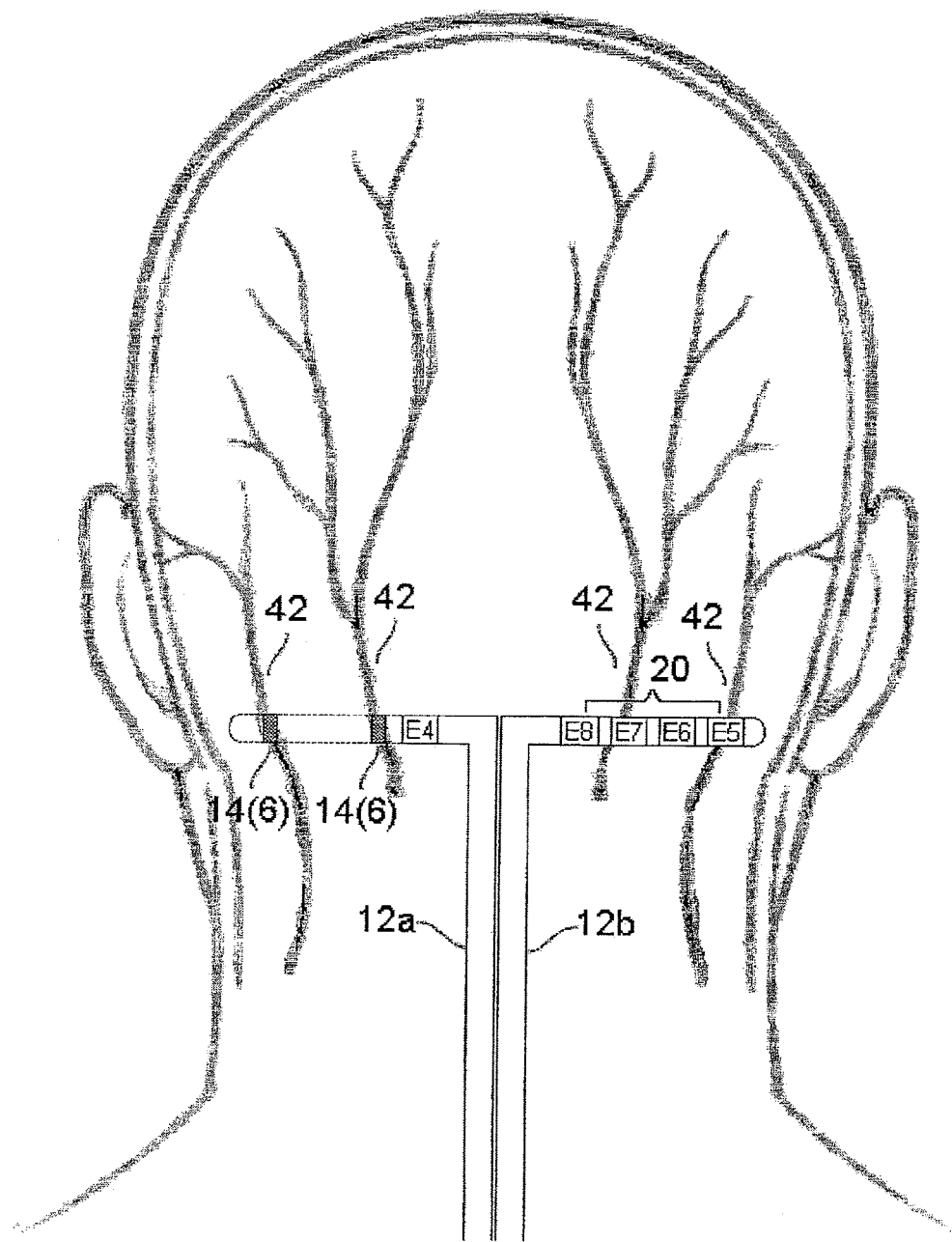
FIG. 8 is a detailed posterior view of two electrode leads and two capacitive sensors of an ONS system arranged in accordance with the present inventions in use with a patient, whose scalp has been rendered transparent for clarity—the distal portion of the electrode lead on the left side of the figure, except for the capacitive sensors, has also been removed for clarity.
Figure 9:
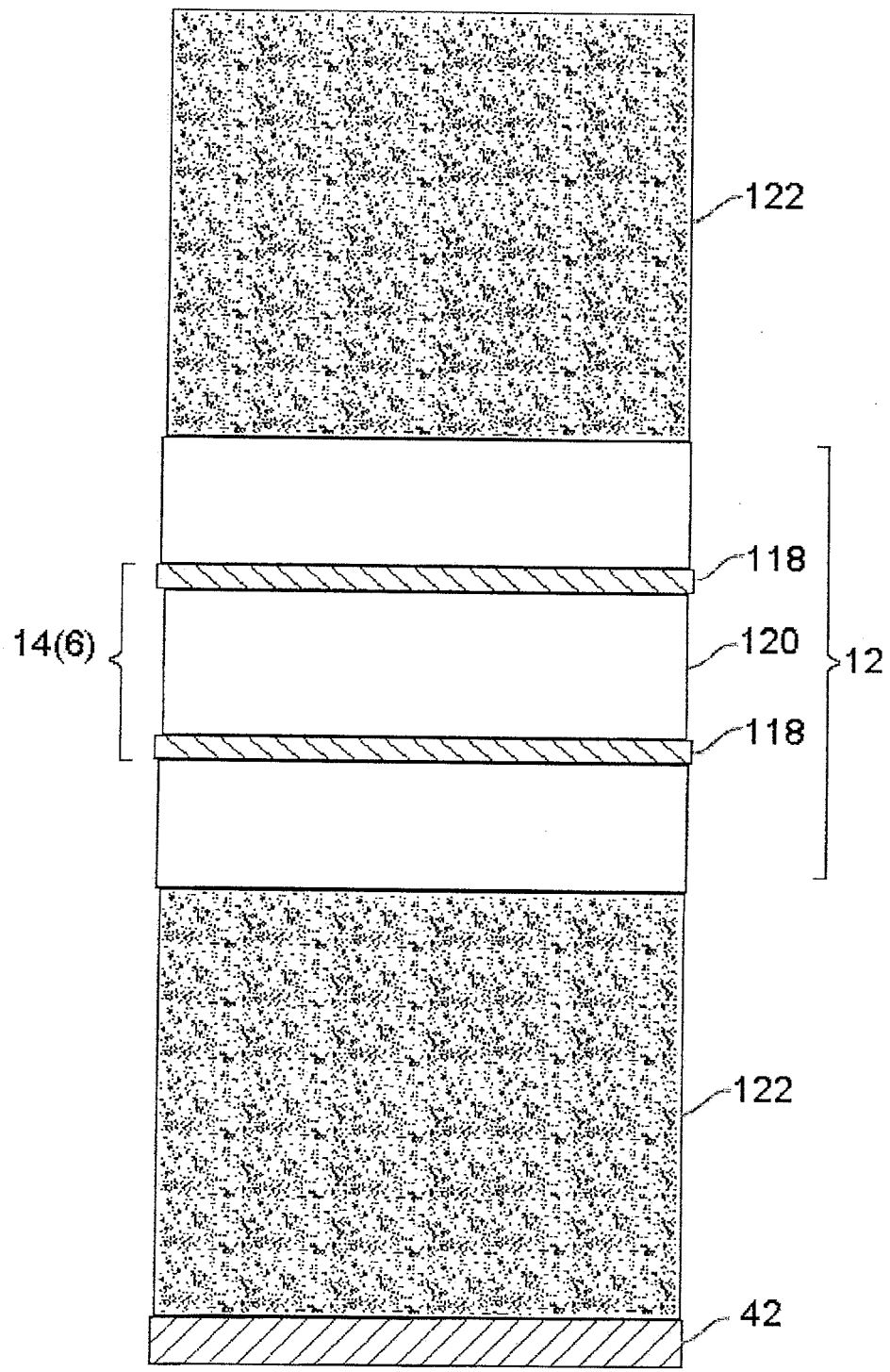
FIG. 9 is a detailed cross sectional view through a capacitive sensor embedded in an electrode lead of an ONS system arranged in accordance with the present inventions in use with a patient.

In still another embodiment, as shown in FIGS. 8 and 9, the monitoring circuitry 58 is configured to monitor the capacitance of capacitive sensors 14(6), which are each formed from two capacitive plates 118 separated by a compressible and/or flexible dielectric material 120 (FIG. 9). The capacitive plates 118 may be flat or they may be curved to conform to the shape of the leads 12. The capacitive sensors 14(6) are embedded within the leads 12. Alternatively, the capacitive sensors 14(6) may be attached to the surfaces of the leads 12 closest to the respective occipital nerves 42. Alternatively, the capacitor may be placed within the leads 12. The capacitive sensors 14(6) are configured to change capacitance when the patient changes posture and the thicknesses of the tissue 122 separating the electrode leads 12 from the respective occipital nerves 42 change. These changes in tissue thickness affect the distance between the two capacitive plates 118 between the electrode leads 12 and the respective occipital nerves 42. Decreasing tissue thickness, which indicates decreased distance between the electrode leads 12 and the respective occipital nerves 42, compresses the compressible dielectric material 120, decreasing the distance between the capacitive plates 118 and resulting in increased capacitance. Increasing tissue thickness, which indicates increased distance between the electrode leads 12 and the respective occipital nerves 42, releases pressure on the compressible dielectric material 120, increasing the distance between the capacitive plates 118 and resulting in decreased capacitance.

Figure 10:
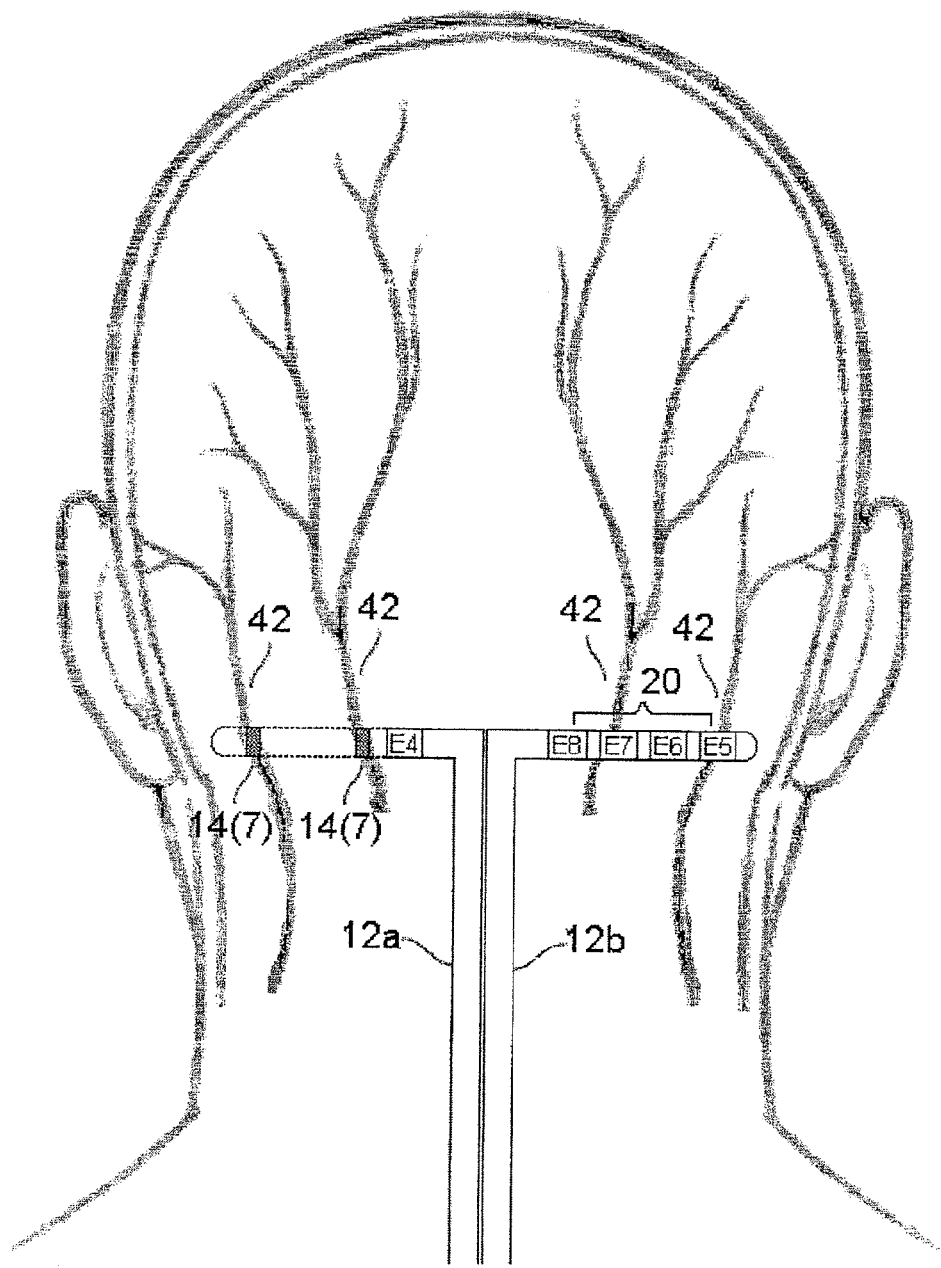
FIG. 10 is a detailed posterior view of two electrode leads and two temperature sensors of an ONS system arranged in accordance with the present inventions in use with a patient, whose scalp has been rendered transparent for clarity—the distal portion of the electrode lead on the left side of the figure, except for the temperature sensors, has also been removed for clarity.

In another embodiment, as shown in FIG. 10, the monitoring circuitry 58 is configured to monitor the temperature at temperature sensors 14(7) embedded within the leads 12. Alternatively, the temperature sensors 14(7) may be ring sensors attached to the surface of the leads 12. The temperature sensors 14(7) are configured to measure changes in temperature when the patient changes posture and the location of electrode leads 12 in the skin of the patient changes. Measured temperature increases as the temperature sensors 14(7) and the electrode leads 12 move deeper into the skin and closer to the occipital nerves 42. In contrast, measured temperature decreases as the temperature sensors 14(7) and the electrode leads 12 move shallower into the skin and away from the occipital nerves 42.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for determining a change in position of a neurostimulation lead relative to a stimulation target tissue of a patient, comprising:
   affixing a first proximity sensor on a surface of the patient;
   affixing a second proximity sensor on the surface of the patient;
   measuring a change in a distance between the first and second proximity sensors; and inferring the change in position of the lead relative to the stimulation target tissue from the measured change in distance.

2. The method of claim 1, further comprising inferring an increase in a distance between the lead and the stimulation target tissue when the distance between the first and second proximity sensors increases.

3. The method of claim 1, further comprising: conveying electrical stimulation energy to therapeutically stimulate the stimulation target tissue; and modulating a stimulation parameter in response to the measured change in distance.

4. The method of claim 3, wherein modulating a stimulation parameter in response to the inferred change in position comprises increasing an amplitude of a stimulation current when the distance between the first and second proximity sensors increases.

5. The method of claim 3, further comprising automatically modulating the stimulation parameter in response to the inferred change in position.

6. The method of claim 3, wherein the step of modulating a stimulation parameter comprises adjusting an amplitude of the stimulus applied to selected electrodes during the conveyance of the stimulation energy.

7. The method of claim 3, further comprising conveying electrical stimulation energy via a combination of electrodes to therapeutically stimulate the stimulation target tissue via electrodes, wherein the step of modulating a stimulation parameter comprises changing the combination of the electrodes.

8. A system for determining a change in position of a neurostimulation lead relative to a stimulation target tissue of a patient, comprising:
   a first proximity sensor configured to be placed on a surface of the patient;
   a second proximity sensor configured to be placed on the surface of the patient;
   monitoring circuitry configured to measure a change in a distance between the first and second proximity sensors; and
   processing circuitry configured to infer the change in position of the lead relative to the stimulation target tissue from the measured change in distance.

9. The system of claim 8, wherein the processing circuitry is configured to infer an increase in a distance between the lead and the stimulation target tissue when the distance between the first and second proximity sensors increases.

10. The system of claim 8, further comprising: an implantable pulse generator configured to be coupled to the lead and to convey electrical stimulation energy to therapeutically stimulate the stimulation target tissue; and control circuitry configured to modulate a stimulation parameter in response to the inferred change in position.

11. The system of claim 10, wherein the control circuitry is configured to increase an amplitude of a stimulation current when the distance between the first and second proximity sensors increases.

12. The system of claim 10, wherein the control circuitry is configured to automatically modulate the stimulation parameter in response to the measured change in distance.

13. The system of claim 10, wherein the control circuitry is configured to adjust an amplitude of the stimulus applied to selected electrodes during the conveyance of the stimulation energy in response to the inferred change in position.

14. The system of claim 10, further comprising a plurality of electrodes configured to be coupled to the lead and to convey electrical stimulation energy to therapeutically stimulate the stimulation target tissue via a combination of electrodes, wherein the control circuitry is configured to change the combination of the electrodes in response to the inferred change in position.

* * * * *